(12) United States Patent
Zhong et al.

(10) Patent No.: US 10,421,902 B2
(45) Date of Patent: Sep. 24, 2019

(54) METHOD OF PREPARING LUMINESCENT NANO-SHEET, LUMINESCENT NANO-SHEET MATERIAL, LUMINESCENT NANO-SHEET FILM, BACK LIGHT, AND LIQUID CRYSTAL DISPLAY APPARATUS

(71) Applicants: BOE TECHNOLOGY GROUP CO., LTD., Beijing (CN); BEIJING INSTITUTE OF TECHNOLOGY, Beijing (CN)

(72) Inventors: Haizheng Zhong, Beijing (CN); Lige Liu, Beijing (CN)

(73) Assignees: BOE TECHNOLOGY GROUP CO., LTD., Beijing (CN); BEIJING INSTITUTE OF TECHNOLOGY, Beijing (CN)

(*) Notice: Subject to any disclaimer, the term of this patent is extended or adjusted under 35 U.S.C. 154(b) by 0 days.

(21) Appl. No.: 15/750,281

(22) PCT Filed: Jun. 21, 2017

(86) PCT No.: PCT/CN2017/089319
§ 371 (c)(1),
(2) Date: Feb. 5, 2018

(87) PCT Pub. No.: WO2018/028312
PCT Pub. Date: Feb. 15, 2018

(65) Prior Publication Data
US 2019/0010393 A1    Jan. 10, 2019

(30) Foreign Application Priority Data
Aug. 12, 2016   (CN) .......................... 2016 1 0665824

(51) Int. Cl.
*C09K 11/66*    (2006.01)
*B82Y 20/00*    (2011.01)
(Continued)

(52) U.S. Cl.
CPC ............ *C09K 11/664* (2013.01); *B82Y 20/00* (2013.01); *C07F 1/08* (2013.01); *C07F 7/22* (2013.01);
(Continued)

(58) Field of Classification Search
CPC ......... C09K 11/664; B82Y 20/00; C07F 1/08; C07F 7/2208; C07F 7/24; C07F 7/30; C07F 9/94; C07F 13/00
See application file for complete search history.

(56) References Cited

U.S. PATENT DOCUMENTS

2017/0233645 A1*   8/2017   Zhong .................... C09K 11/02
                                                                    252/301.16

FOREIGN PATENT DOCUMENTS

| CN | 104388089 A | 3/2015 |
| CN | 104861958 A | 8/2015 |

(Continued)

OTHER PUBLICATIONS

International Search Report & Written Opinion dated Sep. 27, 2017, regarding PCT/CN2017/089319.
(Continued)

*Primary Examiner* — C Melissa Koslow
(74) *Attorney, Agent, or Firm* — Intellectual Valley Law, P.C.

(57) ABSTRACT

The present application discloses a method of preparing a luminescent nano-sheet. The method includes preparing a precursor emulsion solution containing a metal halide and $RNH_3X$, and having a molar ratio of metal halide to $RNH_3X$ in a range of approximately 0.6 to approximately 0.8; demulsifying the precursor emulsion solution to obtain a perovskite quantum dots material and a demulsified solution; and forming the luminescent nano-sheet by allowing the perovskite quantum dots material self-assemble into the (Continued)

luminescent nano-sheet. X is a halide, R is selected from alkyl, alkenyl, alkynyl, cycloalkyl, cycloalkenyl, cycloalkynyl, aryl, heteroaryl, and heterocyclyl.

19 Claims, 3 Drawing Sheets

(51) Int. Cl.
| | |
|---|---|
| C07F 13/00 | (2006.01) |
| C07F 1/08 | (2006.01) |
| C07F 7/22 | (2006.01) |
| C07F 7/24 | (2006.01) |
| C07F 7/30 | (2006.01) |
| C09K 11/02 | (2006.01) |
| C09K 11/06 | (2006.01) |
| G02F 1/1335 | (2006.01) |
| B82Y 40/00 | (2011.01) |
| B82Y 30/00 | (2011.01) |
| C09K 11/57 | (2006.01) |
| C09K 11/58 | (2006.01) |
| C09K 11/74 | (2006.01) |

(52) U.S. Cl.
CPC .............. *C07F 7/24* (2013.01); *C07F 7/30* (2013.01); *C07F 13/00* (2013.01); *C09K 11/02* (2013.01); *C09K 11/06* (2013.01); *G02F 1/13362* (2013.01); *G02F 1/133602* (2013.01); *B82Y 30/00* (2013.01); *B82Y 40/00* (2013.01); *C09K 11/57* (2013.01); *C09K 11/58* (2013.01); *C09K 11/7428* (2013.01); *C09K 2211/188* (2013.01); *G02F 2001/133614* (2013.01); *G02F 2202/36* (2013.01)

(56) References Cited

FOREIGN PATENT DOCUMENTS

| | | | |
|---|---|---|---|
| CN | 105489775 A | | 4/2016 |
| CN | 105621477 A | | 6/2016 |
| CN | 105633189 A | | 6/2016 |
| CN | 105647530 A | | 6/2016 |
| JP | 2014078392 A | | 5/2014 |
| WO | 2015121682 A1 | | 8/2015 |
| WO | 2016070713 A1 | | 5/2016 |
| WO | 2016072807 A1 | | 5/2016 |
| WO | WO 2016/070713 | * | 5/2016 |

OTHER PUBLICATIONS

Emulsion Synthesis of Size-Tunable CH3NH3PbBr3 Quantum Dots: An Alternative Route toward Efficient Light-Emitting Diodes, Huang, Hailong et al., No. 51 vol. 7, ACS Applied Materials & Interfaces, ISSN: 1944-8244 (Mar. 4, 2015).
Assessment of Anisotropic Semiconductor Nanorod and Nanoplatelet Heterostructures with Polarized Emission for Liquid Crystal Display Technology, Cunningham, P. D. et al., ACS Nano 2016, 10 (6), 5769-5781.
Perovskite Crystals for Tunable White Light Emission, Pathak, S. et al., Chem. Mater. 2015, 27 (23), 8066-8075.
Reversible Halide Exchange Reaction of Organometal Trihalide Perovskite Colloidal Nanocrystals for Full-Range Band Gap Tuning, Jang, D. M. et al., Nano lett. 2015, 15(8), 5191-5199.
First Office Action in the Chinese Patent Application No. 201610665824. X, dated Mar. 7, 2019; English translation attached.
Colloidal Organohalide Perovskite Nanoplatelets Exhibiting Quantum Confinement, Pooja Tyagi et al., J. Phys. Chem. Lett. 2015, No. 6, pp. 1911-1916 (May 4, 2015).
Organometal Halide Perovsite Quantum Dots: Synthesis, Optical Properties, and Display Applications, Gao-Ling Yang et al., Chinese Chemical Letters, 2016, No. 27, pp. 1124-1130 (Jul. 11, 2016).

* cited by examiner

METHOD OF PREPARING LUMINESCENT NANO-SHEET, LUMINESCENT NANO-SHEET MATERIAL, LUMINESCENT NANO-SHEET FILM, BACK LIGHT, AND LIQUID CRYSTAL DISPLAY APPARATUS

CROSS-REFERENCE TO RELATED APPLICATION

This application is a national stage application under 35 U.S.C. § 371 of International Application No. PCT/CN2017/089319, filed Jun. 21, 2017, which claims priority to Chinese Patent Application No. 01610665824.X, filed Aug. 12, 2016, the contents of which are incorporated by reference in the entirety.

TECHNICAL FIELD

The present invention relates to quantum dots material, more particularly, to a method of preparing a luminescent nano-sheet, a luminescent nano-sheet material, a luminescent nano-sheet film, a back light, and a liquid crystal display apparatus.

BACKGROUND

Perovskite materials are materials that are capable of having a perovskite type crystal structure (e.g., a same type of crystal structure as calcium titanium oxide). Perovskite materials can exist in a perovskite crystalline phase regardless of whether the material is actually in such phase. Some perovskite materials have the general stoichiometry AMX3, where "A" and "M" are cations and "X" is an anion. The "A" and "M" cations can have a variety of charges. The anions may be the same or different. The perovskite materials may include structures having three or four anions, which may be the same or different, and two metal atoms carrying two or three positive charges. Examples of perovskite materials include $CH_3NH_3PbX_3$, wherein $X_3$ are three halide anions selected from Cl, Br and I, or any combination thereof.

SUMMARY

In one aspect, the present invention provides a method of preparing a luminescent nano-sheet, comprising preparing a precursor emulsion solution comprising a metal halide and $RNH_3X$, and having a molar ratio of metal halide to $RNH_3X$ in a range of approximately 0.6 to approximately 0.8; demulsifying the precursor emulsion solution to obtain a perovskite quantum dots material and a demulsified solution; and forming the luminescent nano-sheet by allowing the perovskite quantum dots material self-assemble into the luminescent nano-sheet; wherein X is a halide, R is selected from alkyl, alkenyl, alkynyl, cycloalkyl, cycloalkenyl, cycloalkynyl, aryl, heteroaryl, and heterocyclyl.

Optionally, preparing the precursor emulsion solution comprises preparing a $RNH_3X$ solution in a first solvent, the $RNH_3X$ solution having a $RNH_3X$ concentration greater than approximately 0.5 mol/L; preparing a metal halide solution in a second solvent, each of the second solvent and the first solvent comprises a same polar solvent; dispensing the $RNH_3X$ solution and the metal halide solution into an emulsion solution; and homogenizing a mixture comprising the $RNH_3X$ solution, the metal halide solution, and the emulsion solution to obtain the precursor emulsion solution.

Optionally, the emulsion solution comprises an organic acid, or an organic amine, or a combination of an organic acid and an organic amine.

Optionally, the emulsion solution comprises n-hexane, an organic acid, and an organic amine.

Optionally, the $RNH_3X$ solution has a $RNH_3X$ concentration greater than approximately 1.06 mol/L.

Optionally, forming the luminescent nano-sheet comprises allowing the perovskite quantum dots material to stand in the demulsified solution for a duration equal to or greater than approximately 30 minutes.

Optionally, forming the luminescent nano-sheet comprises allowing the perovskite quantum dots material to stand in the demulsified solution at a temperature in a range of approximately −30 degrees Celsius to approximately 70 degrees Celsius.

Optionally, forming the luminescent nano-sheet comprises separating the perovskite quantum dots material from the demulsified solution; dispersing the perovskite quantum dots material into a non-polar organic solvent; and allowing the perovskite quantum dots material to stand in the non-polar organic solvent for a duration equal to or greater than approximately 30 minutes.

Optionally, allowing the perovskite quantum dots material to stand in the non-polar organic solvent comprises allowing the perovskite quantum dots material to stand in the non-polar organic solvent for a duration equal to or less than approximately 72 hours.

Optionally, the non-polar organic solvent comprises one or a combination of toluene, n-hexane, n-heptane, cyclohexane, and tetrahydrofuran.

Optionally, allowing the perovskite quantum dots material to stand in the non-polar organic solvent comprises allowing the perovskite quantum dots material to stand in the non-polar organic solvent at a temperature in a range of approximately −30 degrees Celsius to approximately 70 degrees Celsius.

Optionally, dispersing the perovskite quantum dots material into the non-polar organic solvent is performed so that a concentration of the perovskite quantum dots material in the non-polar organic solvent is a range of approximately 1.0 mg/ml to approximately 3.5 mg/ml.

Optionally, demulsifying the precursor emulsion solution comprises demulsifying the precursor emulsion solution with a demulsifier, and the demulsifier comprises acetone, or $C_nH_{2n+1}OH$, n≥1, or a combination thereof.

Optionally, each of the second solvent and the first solvent comprises N, N-dimethylformamide.

Optionally, the metal halide comprises germanium halide, tin halide, lead halide, bismuth halide, copper halide, or manganese halide.

Optionally, the metal halide comprises lead bromide, the $RNH_3X$ comprises $RNH_3Br$, and the luminescent nano-sheet comprises $RNH_3PbBr_3$.

In another aspect, the present invention provides a luminescent nano-sheet material, comprising a plurality of luminescent nano-sheets; wherein a thickness of the plurality of luminescent nano-sheets is in a range of approximately 3 nm to approximately 6 nm; and a width of the plurality of luminescent nano-sheets is in a range of approximately 10 nm to approximately 1000 nm.

Optionally, the luminescent nano-sheet material has an emission peak between approximately 510 nm and approximately 530 nm with a half-width in a range of approximately 20 nm to approximately 30 nm and the luminescent nano-sheet material, upon excitation, emits a fluorescent light having a fluorescence quantum yield between approximately 50% and approximately 90%, and a fluorescence life between approximately 25.4 nanoseconds and approximately 40 nanoseconds.

In another aspect, the present invention provides a luminescent nano-sheet film, comprising a transparent organic matrix; and the luminescent nano-sheet material described herein, dispersed in the transparent organic matrix; wherein the luminescent nano-sheet material comprises a plurality of luminescent nano-sheets substantially aligned in the transparent organic matrix.

Optionally, the luminescent nano-sheet film comprises a plurality of pixel areas, each of which comprising a red sub-pixel area, a green sub-pixel area, and a blue sub-pixel area; the luminescent nano-sheet film in the red sub-pixel area comprises a luminescent nano-sheet prepared from a precursor comprising $RNH_3I$; the luminescent nano-sheet film in the green sub-pixel area comprises a luminescent nano-sheet prepared from a precursor comprising $RNH_3Br$; and the luminescent nano-sheet film in the blue sub-pixel area comprises a luminescent nano-sheet prepared from a precursor comprising $RNH_3Cl$.

Optionally, the transparent organic matrix comprises poly-4-methyl-pentene.

In another aspect, the present invention provides a back light comprising the luminescent nano-sheet film described herein and a laser light source configured to excite the luminescent nano-sheet film to emit light.

Optionally, the laser light source is a laser light source configured to emit blue light.

In another aspect, the present invention provides a liquid crystal display apparatus, comprising the back light described herein and a liquid crystal display panel.

BRIEF DESCRIPTION OF THE FIGURES

The following drawings are merely examples for illustrative purposes according to various disclosed embodiments and are not intended to limit the scope of the present invention.

DETAILED DESCRIPTION

The disclosure will now be described more specifically with reference to the following embodiments. It is to be noted that the following descriptions of some embodiments are presented herein for purpose of illustration and description only. It is not intended to be exhaustive or to be limited to the precise form disclosed.

Typically, a conventional liquid crystal display apparatus includes a liquid crystal display panel having a liquid crystal layer, a first polarizer on a light incident side of the liquid crystal display panel, and a second polarizer on a light emitting side of the liquid crystal display panel. To achieve color display, the conventional liquid crystal display panel typically includes an array substrate and a color filter substrate facing the array substrate. Thus, the conventional liquid crystal display apparatus has a relatively complicated structure.

Conventional methods for making nano-sheets typically require a high-temperature and high-pressure environment, and are energy consuming. Moreover, the nano-sheets fabricated by conventional methods typically have a relatively low purity, and often include a large amount of quantum dots.

Accordingly, the present disclosure provides, inter alia, a method of preparing a luminescent nano-sheet, a luminescent nano-sheet material, a luminescent nano-sheet film, a back light, and a liquid crystal display apparatus that substantially obviate one or more of the problems due to limitations and disadvantages of the related art. In one aspect, the present disclosure provides a method of preparing a luminescent nano-sheet. In some embodiments, the method includes preparing a precursor emulsion solution comprising a metal halide and $RNH_3X$, X is a halide, and having a molar ratio of metal halide to $RNH_3X$ in a range of approximately 0.6 to approximately 0.8; demulsifying the precursor emulsion solution to obtain a perovskite quantum dots material and a demulsified solution; and forming the luminescent nano-sheet by allowing the perovskite quantum dots material self-assemble into the luminescent nano-sheet. Optionally, R is selected from alkyl, alkenyl, alkynyl, cycloalkyl, cycloalkenyl, cycloalkynyl, aryl, heteroaryl, heterocyclyl. Optionally, R is alkyl. Optionally, R is methyl.

In some embodiments, the metal cation in the metal halide is selected from metal element of Groups IIIB, IVB, VB, VIB, VIIB, VIIIB, IB, IIB, IIIA, IVA, and VA of block d of the periodic table of the elements. Optionally, the metal cation in the metal halide is a transition metal selected from Groups IIIB, IVB, VB, VIB, VIIB, VIIIB, IB and IIB of block d of the periodic table. Optionally, the transition metal is a metal selected from Sc, Ti, V, Cr, Mn, Fe, Ni, Cu, Zn, Y, Zr, Nb, Tc, Ru, Mo, Rh, W, Au, Pt, Pd, Ag, Mn, Co, Cd, Hf, Ta, Re, Os, Ir, Hg, or any combination thereof. Optionally, the metal cation in the metal halide is a post-transition metal selected from Groups IIIA, IVA, and VA. Optionally, the metal cation is a metal element selected from Al, Ga, In, Ti, Sn, Pb, Bi, or any combination thereof. Optionally, the metal cation in the metal halide is a semi-metal selected from Groups IIIA, IVA, VA, and VIA. Optionally, the metal cation is a metal element selected from B, Si, Ge, As, Sb, Po, or any combination thereof. Optionally, the metal cation in the metal halide is an alkali metal selected from Group IA. Optionally, the metal cation is an alkali metal element selected from Li, Mg, Na, K, Rb, Cs, or any combination thereof. Optionally, the metal cation in the metal halide is an alkaline earth metal selected from Group IIA. Optionally, the metal cation is an element selected from Be, Ca, Sr, Ba, or any combination thereof. Optionally, the metal cation in the metal halide is a lanthanide element. Optionally, the metal cation is an element selected from Ce, Pr, Gd, Eu, Tb, Dy, Er, Tm, Nd, Yb, or any combination thereof. Optionally, the metal cation in the metal halide is an actinide element. Optionally, the metal cation is an element selected from Ac, Th, Pa, U, Np, Pu, Am, Cm, Bk, Cf, Es, Fm, Md, No, Lr, or any combination thereof. Optionally, the metal cation in the metal halide is a divalent metal element. Optionally, the metal cation is an element selected from $Cu^{2+}$, $Ni^{2+}$, $Cd^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $Eu^{2+}$, $Yb^{2+}$, or any combination thereof. Optionally, the metal cation in the metal halide is a trivalent metal element. Optionally, the metal cation is an element selected from $Bi^{3+}$, $Sb^{3+}$, or any combination thereof. Optionally, the metal cation in the metal halide is a metal element selected from Ge, Sn, Pb, Bi, Cu, Mn, or any combination thereof. Optionally, the metal cation is $Pb^{2+}$.

As used herein, the term "nano-sheet" refers to particles that are sheet-like in shape and have any dimension in the nanometer to micrometer range. For example, the nano-sheets are particles that are relatively thin in one dimension (e.g., z dimension) and have a relatively large area in another two dimensions (e.g., x and y dimensions). Optionally, the nano-sheets have a thickness in the range of approximately 0.5 nm to approximately 15 nm, an average width in the range of approximately 5 nm to approximately 10 μm, and an average length in the range of approximately 5 nm to approximately 10 μm. Optionally, the nano-sheets have a thickness in the range of approximately 1 nm to approximately 10 nm, an average width in the range of approximately 5 nm to approximately 5 μm, and an average length in the range of approximately 5 nm to approximately 5 μm. Optionally, the nano-sheets have a thickness in the range of approximately 3 nm to approximately 6 nm, an average width in the range of approximately 10 nm to approximately 1000 nm, and an average length in the range of approximately 10 nm to approximately 1000 nm. Optionally, the nano-sheets have an aspect ratio (width to thickness or length to thickness) in the range of approximately 2 to approximately 500, e.g., approximately 2 to approximately 50, approximately 50 to approximately 100, approximately 100 to approximately 500, or approximately 2 to approximately 350.

The quantum dots materials prepared using a $RNH_3X$ and a metal halide (e.g., an inorganic metal halide) includes a core and surface ligands. The surface ligands emanate from the core, and cover the surface of the core. In one example, the core includes $R_1NH_3AB_3$ or $(R_2NH_3)_2AB_4$, wherein A and B form a coordination octahedral structure, and $R_1NH_3$ or $R_2NH_3$ molecules fills in coordination octahedral gaps. Optionally, $R_1$ is a methyl. Optionally, $R_2$ is a long-chain organic group. Optionally, A is a metal cation in the metal halide (e.g., an inorganic metal halide). Optionally. B is a halide. Optionally, the surface ligand is an organic acid or an organic amine (e.g., a long-chain organic amine). The molecule structure of the core of the quantum dots is conducive to the formation of strong dipole moments. Through the interaction of dipole moments, the quantum dots are capable of self-assembling. Moreover, the perovskite quantum dots material includes surface ligands on the surface, enhancing the interaction between the molecules thereby facilitating the self-assembling process.

In some embodiments, the step of preparing the precursor emulsion solution includes preparing a $RNH_3X$ (e.g. $CH_3NH_3X$) solution in a first solvent, the $RNH_3X$ solution having a $RNH_3X$ concentration greater than approximately 0.5 mol/L (e.g., greater than approximately 0.53 mol/L); preparing a metal halide solution in a second solvent, each of the second solvent and the first solvent comprises a same polar solvent; dispensing the $RNH_3X$ solution and the metal halide solution into an emulsion solution; and homogenizing a mixture having the $RNH_3X$ solution, the metal halide solution, and the emulsion solution to obtain the precursor emulsion solution.

Optionally, the $RNH_3X$ (e.g. $CH_3NH_3X$) solution has a concentration greater than approximately 0.5 mol/L and equal to or less than a saturation concentration. Optionally, the $RNH_3X$ solution has a concentration greater than approximately 0.6 mol/L. Optionally, the $RNH_3X$ solution has a concentration greater than approximately 0.7 mol/L. Optionally, the $RNH_3X$ solution has a concentration greater than approximately 0.8 mol/L. Optionally, the $RNH_3X$ solution has a concentration greater than approximately 0.9 mol/L. Optionally, the $RNH_3X$ solution has a concentration greater than approximately 1.0 mol/L. Optionally, the $RNH_3X$ solution has a concentration greater than approximately 1.06 mol/L. Optionally, the $RNH_3X$ (e.g. $CH_3NH_3X$) solution is a super-saturated solution.

In the present method, a high concentration $RNH_3X$ (e.g. $CH_3NH_3X$) solution and a high concentration metal halide solution are used. Accordingly, subsequent to the demulsifying step, a demulsified solution having a high concentration perovskite quantum dots can be obtained, facilitating the self-assembling process of the perovskite quantum dots.

Various appropriate conditions may be used to allow the perovskite quantum dots material self-assemble into the luminescent nano-sheet. In one example, the demulsified solution contains the perovskite quantum dots in a sufficiently high concentration such that the perovskite quantum dots automatically self-assemble into the luminescent nano-sheet simultaneously or concurrently during the demulsifying step. In another example, the demulsified solution containing the perovskite quantum dots material is allowed to stand for a period of time, thereby allowing the quantum dots self-assemble sufficiently into the luminescent nano-sheet. In another example, the perovskite quantum dots material is transferred into a non-polar solvent, and is allowed to stand for a period of time.

In some embodiments, the emulsion solution used for preparing the precursor emulsion solution includes an organic material. Optionally, the emulsion solution includes an organic acid. Optionally, the emulsion solution includes a saturated organic acid, e.g., $C_nH_{2n+1}COOH$ (n≥2). Optionally, the emulsion solution includes an unsaturated organic acid, e.g., $C_nH_{2n-1}COOH$ (n≥2). Optionally, the emulsion solution includes an organic amine, e.g., a long-chain organic amine.

Optionally, the emulsion solution further includes an organic solvent such as an alkane, e.g., n-hexane. The alkane (e.g., n-hexane) facilitates the dissolvation of the organic acid and organic amine in the emulsion solution. Optionally, the emulsion solution includes n-hexane, an organic acid, and an organic amine (e.g., a long-chain organic amine).

Optionally, the method further includes filtering a solution containing the luminescent nano-sheet thereby obtaining a luminescent nano-sheet solid material.

The present luminescent nano-sheet is made by self-assembling the perovskite quantum dots material. Thus, the luminescent nano-sheet has the characteristics of the quantum dots light emitting material. Upon excitation of a laser light, the luminescent nano-sheet emits light, e.g., light of color. Optionally, the luminescent nano-sheet has a thickness in a range of approximately 3 nm to approximately 6 nm, and a width in a range of approximately 10 nm to approximately 1000 nm. Accordingly, the luminescent nano-sheet is anisotropic. Upon excitation by a laser light, the luminescent nano-sheet emits polarized light, e.g., polarized light of color. The present luminescent nano-sheet has very good polarization properties. Optionally, the luminescent nano-sheet has a degree of polarization of 0.11 or more.

Because the present luminescent nano-sheet can emit a polarized light of color, a display apparatus having the present luminescent nano-sheet obviates the needs of a polarizer or even a color filter. The structure of the display apparatus can be greatly simplified.

Figure 1:
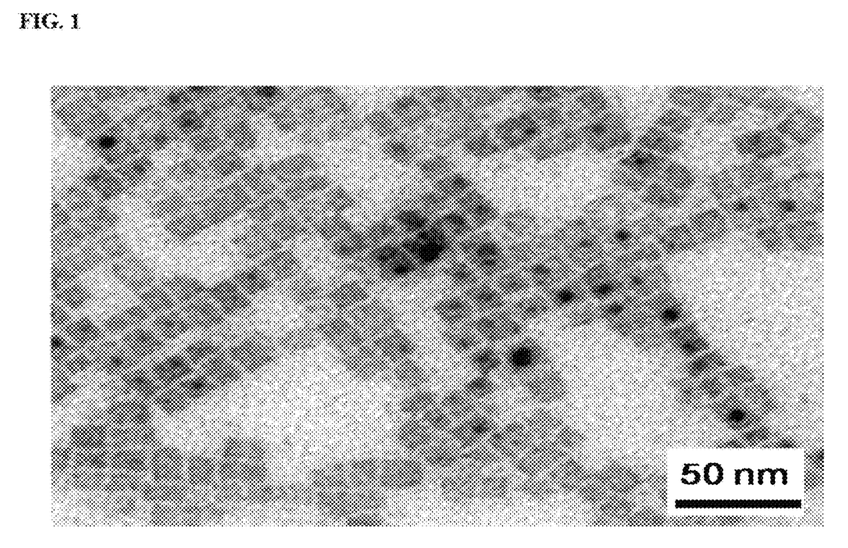
FIG. 1 is a TEM photography of a luminescent nano-sheet prepared in Example IV.

FIG. 1 is a TEM photography of a luminescent nano-sheet in some embodiments according to the present disclosure.

As shown in FIG. 1, the surface of the nano luminescent nano-sheet is substantially free of quantum dots, indicating that the luminescent nano-sheet is of high purity.

In some embodiments, the demulsified solution contains the perovskite quantum dots in a sufficiently high concentration such that the perovskite quantum dots automatically self-assemble into the luminescent nano-sheet simultaneously or concurrently during the demulsifying step. Optionally, the $RNH_3X$ (e.g., $CH_3NH_3X$) solution used for preparing the precursor emulation solution has a concentration greater than approximately 1.06 mol/L (and optionally equal to or less than a saturation concentration).

In some embodiments, the step of forming the luminescent nano-sheet includes allowing the perovskite quantum dots material to stand in the demulsified solution for a duration equal to or greater than approximately 30 minutes. The yield of the luminescent nano-sheet can be enhanced by allowing some time for the perovskite quantum dots material to self-assemble. Optionally, the step of forming the luminescent nano-sheet includes allowing the perovskite quantum dots material to stand in the demulsified solution at a temperature in a range of approximately −30 degrees Celsius to approximately 70 degrees Celsius.

In some embodiments, the step of forming the luminescent nano-sheet includes separating the perovskite quantum dots material from the demulsified solution; dispersing the perovskite quantum dots material into a non-polar organic solvent; and allowing the perovskite quantum dots material to stand in the non-polar organic solvent for a duration equal to or greater than approximately 30 minutes. Optionally, the $RNH_3X$ (e.g., $CH_3NH_3X$) solution used for preparing the precursor emulsion solution has a $RNH_3X$ concentration in a range between approximately 0.5 mol/L and approximately 1.06 mol/L. Optionally, the step of allowing the perovskite quantum dots material to stand in the non-polar organic solvent includes allowing the perovskite quantum dots material to stand in the non-polar organic solvent for a duration equal to or less than approximately 72 hours.

In some embodiments, the non-polar organic solvent includes one or a combination of toluene, n-hexane, n-heptane, cyclohexane, and tetrahydrofuran. The perovskite quantum dots material is homogeneously dispersed in the non-polar organic solvent, allowing the perovskite quantum dots material self-assemble into the luminescent nano-sheet. Moreover, the alkane (e.g., n-hexane) provides an excellent dispersion environment for the perovskite quantum dots material, facilitating the self-assembly of the perovskite quantum dots material into the luminescent nano-sheet.

Various appropriate demulsifier may be used for demulsifying the precursor emulsion solution. Examples of demulsifiers includes acetone and $C_nH_{2n+1}OH$, $n≥1$. Optionally, the demulsifier includes acetone. Optionally, the demulsifier includes $CH_2H_{2n+1}OH$, $n≥1$, e.g., methanol, ethanol, isopropanol, or a combination thereof. Optionally, the demulsifier includes acetone and $C_nH_{2n+1}OH$, $n≥1$.

In some embodiments, the solvent used for preparing the $RNH_3X$ (e.g., $CH_3NH_3X$) solution includes N, N-dimethylformamide. Optionally, the solvent used for preparing the metal halide solution includes N, N-dimethylformamide.

Various appropriate metal halide may be used for preparing the present luminescent nano-sheet. Examples of metal halide include germanium halide, tin halide, lead halide, bismuth halide, copper halide, manganese halide, or a combination thereof.

Optionally, the metal halide includes lead halide, the $RNH_3X$ (e.g., $CH_3NH_3X$) includes $RNH_3Br$ (e.g., $CH_3NH_3Br$), and the luminescent nano-sheet includes $RNH_3PbBr_3$ (e.g., $CH_3NH_3PbBr_3$). Upon excitation of a blue laser light, the $RNH_3PbBr_3$ luminescent nano-sheet emits green fluorescent light. The green fluorescent light emitted by the present luminescent nano-sheet is characterized by an emission peak between approximately 510 nm and approximately 530 nm with a relatively narrow half-width, e.g., in a range of approximately 20 nm to approximately 30 nm. Moreover, the fluorescent light has a relatively high fluorescence quantum yield, e.g., between 50% and 90%, and a relatively long fluorescence life, e.g., between 25.4 nanoseconds and 40 nanoseconds. Thus, the present luminescent nano-sheet possesses excellent light emission properties, suitable for making optoelectronic apparatuses.

Optionally, the $RNH_3X$ (e.g., $CH_3NH_3X$) includes $RNH_3I$ (e.g., $CH_3NH_3I$). Upon excitation of a blue laser light, the luminescent nano-sheet prepared using $RNH_3I$ (e.g., $CH_3NH_3I$) emits red fluorescent light. Optionally, the $RNH_3X$ (e.g., $CH_3NH_3X$) includes $RNH_3Cl$ (e.g., $CH_3NH_3Cl$). Upon excitation of a blue laser light, the luminescent nano-sheet prepared using $RNH_3Cl$ (e.g., $CH_3NH_3Cl$) emits blue fluorescent light.

In some embodiments, the perovskite quantum dots material is allowed to stand in a solution at a temperature in a range of approximately −30 degrees Celsius to approximately 70 degrees Celsius. In this temperature range, the perovskite quantum dots material and the luminescent nano-sheet remain relatively stable. Optionally, the perovskite quantum dots material is allowed to stand in the non-polar organic solvent at a temperature in a range of approximately −30 degrees Celsius to approximately 70 degrees Celsius.

Optionally, the perovskite quantum dots material is dispersed into the non-polar organic solvent so that a concentration of the perovskite quantum dots material in the non-polar organic solvent is a range of approximately 1.0 mg/ml to approximately 3.5 mg/ml.

In another aspect, the present disclosure provides a luminescent nano-sheet material having a luminescent nano-sheet fabricated by the method described herein. Optionally, the luminescent nano-sheet material include a luminescent nano-sheet having a cubic crystal phase and a Pm3m space group (No. 221). Optionally, the luminescent nano-sheet has a thickness in a range of approximately 3 nm to approximately 6 nm, and a width in a range of approximately 10 nm to approximately 1000 nm.

In another aspect, the present disclosure provides a luminescent nano-sheet film including a transparent organic matrix and a luminescent nano-sheet material dispersed in the transparent organic matrix. Optionally, the luminescent nano-sheet material includes a plurality of luminescent nano-sheets substantially aligned in the transparent organic matrix. Optionally, the transparent organic matrix is made by polymerizing the non-polar organic solvent used for dispersing the perovskite quantum dots material.

By having the plurality of luminescent nano-sheets substantially aligned in the transparent organic matrix, the luminescent nano-sheet film is capable of emitting polarized light of color upon excitation of a laser light. Accordingly, the present luminescent nano-sheet film can be used in a back light of a liquid crystal display apparatus, obviating the needs for a polarizer and a color filter. The structure of the display apparatus can be greatly simplified.

In some embodiments, the luminescent nano-sheet film includes a plurality of pixel areas. Optionally, each of the plurality of pixel areas includes a red sub-pixel area, a green sub-pixel area, and a blue sub-pixel area. Optionally, the luminescent nano-sheet film in the red sub-pixel area includes a red light emitting luminescent nano-sheet, e.g., one prepared from a precursor including $RNH_3I$ (e.g., $CH_3NH_3I$). Optionally, the luminescent nano-sheet film in the green sub-pixel area includes a green light emitting luminescent nano-sheet, e.g., one prepared from a precursor including $RNH_3Br$ (e.g., $CH_3NH_3Br$). Optionally, the luminescent nano-sheet film in the blue sub-pixel area includes a blue light emitting luminescent nano-sheet, e.g., one prepared from a precursor including $RNH_3Cl$ (e.g., $CH_3NH_3Cl$).

Various appropriate transparent organic materials may be used for making the organic matrix. Optionally, the transparent organic matrix includes poly-4-methyl-pentene.

In another aspect, the present disclosure provides a back light having the luminescent nano-sheet film described herein; and a laser light source configured to excite the luminescent nano-sheet film to emit light. Optionally, the laser light source is a laser light source configured to emit blue light. The back light having the luminescent nano-sheet film is capable of emitting polarized light of color upon excitation of a laser light. Thus, a display apparatus having the present back light obviates the needs for a polarizer and a color filter. The structure of the display apparatus can be greatly simplified.

In another aspect, the present disclosure provides a liquid crystal display apparatus having a back light described herein and a liquid crystal display panel. The back light in the present liquid crystal display apparatus is capable of emitting polarized light of color upon excitation of a laser light. Thus, the present liquid crystal display apparatus obviates the needs for a polarizer and a color filter. The structure of the liquid crystal display apparatus can be greatly simplified. Examples of appropriate liquid crystal display apparatuses include, but are not limited to, an electronic paper, a mobile phone, a tablet computer, a television, a monitor, a notebook computer, a digital album, a GPS, etc.

The following examples are intended to further describe and illustrate various aspects of the disclosure, but not to limit, the scope of the disclosure in any manner, shape, or form, either explicitly or implicitly.

EXAMPLE I

Preparation of a $CH_3NH_3PbBr_3$ Luminescent Nano-sheet

Step 1: In a 5 ml isotope flask, 0.32 mmol $CH_3NH_3Br$ and 0.3 ml N, N-dimethylformamide were added. The $CH_3NH_3Br$ solution was homogenized using ultrasound. In another 5 ml isotope flask, 0.40 mmol lead bromide and 1.0 ml N, N-dimethylformamide were added. The lead bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the lead bromide solution were drop-wisely added to the emulsion solution using a micro-sampler to obtain a precursor emulsion solution.

Step 4: Into the precursor emulsion solution, 8 ml acetone was added to demulsify the precursor emulsion solution. The demulsified solution was transferred to a centrifuge tube and was centrifuged at 7000 rpm for 5 minutes. The supernatant was discarded, thereby obtaining a pellet containing a $CH_3NH_3PbBr_3$ luminescent nano-sheet.

EXAMPLE II

Preparation of a $CH_3NH_3PbBr_3$ Luminescent Nano-sheet

Step 1: In a 5 ml isotope flask, 0.96 mmol $CH_3NH_3Br$ and 0.3 ml N, N-dimethylformamide were added. The $CH_3NH_3Br$ solution was homogenized using ultrasound. In another 5 ml isotope flask, 0.60 mmol lead bromide and 1.5 ml N, N-dimethylformamide were added. The lead bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the lead bromide solution were drop-wisely added to the emulsion solution using a micro-sampler to obtain a precursor emulsion solution.

Step 4: Into the precursor emulsion solution, 8 ml acetone was added to demulsify the precursor emulsion solution. The demulsified solution was transferred to a centrifuge tube and was centrifuged at 7000 rpm for 5 minutes. The supernatant was discarded, thereby obtaining a pellet containing a $CH_3NH_3PbBr_3$ luminescent nano-sheet.

EXAMPLE III

Preparation of a $CH_3NH_3PbBr_3$ Luminescent Nano-sheet

Step 1: In a 5 ml isotope flask, 0.32 mmol $CH_3NH_3Br$ and 0.3 ml N, N-dimethylformamide were added. The $CH_3NH_3Br$ solution was homogenized using ultrasound. In another 5 ml isotope flask, 0.40 mmol lead bromide and 1.0 ml N, N-dimethylformamide were added. The lead bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the lead bromide solution were drop-wisely added to the emulsion solution using a micro-sampler to obtain a precursor emulsion solution.

Step 4: Into the precursor emulsion solution, 8 ml acetone was added to demulsify the precursor emulsion solution. The demulsified solution was allowed to stand still at 60 degrees Celsius for 1 hour. The resulting solution was transferred to a centrifuge tube and was centrifuged at 7000 rpm for 5 minutes. The supernatant was discarded, thereby obtaining a pellet containing a $CH_3NH_3PbBr_3$ luminescent nano-sheet.

EXAMPLE IV

Preparation of a $CH_3NH_3PbBr_3$ Luminescent Nano-sheet

Step 1: In a 5 ml isotope flask, 0.16 mmol $CH_3NH_3Br$ and 0.3 ml N,N-dimethylformamide were added. The $CH_3NH_3Br$ solution was homogenized using ultrasound. In another 5 ml isotope flask, 0.20 mmol lead bromide and 1.0 ml N, N-dimethylformamide were added. The lead bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the lead bromide solution were drop-wisely added to the emulsion solution using a micro-sampler to obtain a precursor emulsion solution.

Step 4: Into the precursor emulsion solution, 8 ml acetone was added to demulsify the precursor emulsion solution. The demulsified solution was allowed to stand still at 30 degrees Celsius for 24 hours. The resulting solution was transferred to a centrifuge tube and was centrifuged at 7000 rpm for 5 minutes. The supernatant was discarded, thereby obtaining a pellet containing a $CH_3NH_3PbBr_3$ luminescent nano-sheet.

EXAMPLE V

Preparation of a $CH_3NH_3SnBr_3$ Luminescent Nano-sheet

Step 1: In a 5 ml isotope flask, 0.6 mmol $CH_3NH_3Br$ and 0.3 ml N, N-dimethylformamide were added. The $CH_3NH_3Br$ solution was homogenized using ultrasound. In another 5 ml isotope flask, 0.20 mmol tin bromide and 1.0 ml N, N-dimethylformamide were added. The tin bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the tin bromide solution were drop-wisely added to the emulsion solution using a micro-sampler to obtain a precursor emulsion solution.

Step 4: Into the precursor emulsion solution, 8 ml acetone was added to demulsify the precursor emulsion solution. The demulsified solution was allowed to stand still at 0 degrees Celsius for 48 hours. The resulting solution was transferred to a centrifuge tube and was centrifuged at 7000 rpm for 5 minutes. The supernatant was discarded, thereby obtaining a pellet containing a $CH_3NH_3PbBr_3$ luminescent nano-sheet.

EXAMPLE VI

Preparation of a $CH_3NH_3PbBr_3$ Luminescent Nano-sheet

Step 1: In a 5 ml isotope flask, 0.16 mmol $CH_3NH_3Br$ and 0.3 ml N, N-dimethylformamide were added. The $CH_3NH_3Br$ solution was homogenized using ultrasound. In another 5 ml isotope flask, 0.20 mmol lead bromide and 1.0 ml N, N-dimethylformamide were added. The lead bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the lead bromide solution were drop-wisely added to the emulsion solution using a micro-sampler to obtain a precursor emulsion solution.

Step 4: Into the precursor emulsion solution, 8 ml acetone was added to demulsify the precursor emulsion solution. The demulsified solution was allowed to stand still at −30 degrees Celsius for 72 hours. The resulting solution was transferred to a centrifuge tube and was centrifuged at 7000 rpm for 5 minutes. The supernatant was discarded, thereby obtaining a pellet containing a $CH_3NH_3PbBr_3$ luminescent nano-sheet.

EXAMPLE VII

Preparation of a $CH_3NH_3MnBr_3$ Luminescent Nano-sheet

Step 1: In a 5 ml isotope flask, 0.16 mmol $CH_3NH_3Br$ and 0.3 ml N, N-dimethylformamide were added. The $CH_3NH_3Br$ solution was homogenized using ultrasound. In another 5 ml isotope flask, 0.20 mmol manganese bromide and 1.0 ml N, N-dimethylformamide were added. The manganese bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the manganese bromide solution were drop-wisely added to the emulsion solution using a micro-sampler to obtain a precursor emulsion solution.

Step 4: Into the precursor emulsion solution, 8 ml acetone was added to demulsify the precursor emulsion solution. The demulsified solution was allowed to stand still at 60 degrees Celsius for 1 hour. The resulting solution was transferred to a centrifuge tube and was centrifuged at 7000 rpm for 5 minutes. The supernatant was discarded, thereby obtaining a pellet containing a $CH_3NH_3PbBr_3$ luminescent nano-sheet.

EXAMPLE VIII

Preparation of a $CH_3NH_3PbBr_3$ Luminescent Nano-sheet

Step 1: In a 5 ml isotope flask, 0.32 mmol $CH_3NH_3Br$ and 0.3 ml N, N-dimethylformamide were added. The $CH_3NH_3Br$ solution was homogenized using ultrasound. In another 5 ml isotope flask, 0.40 mmol lead bromide and 1.0 ml N, N-dimethylformamide were added. The lead bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the lead bromide solution were drop-wisely added to the emulsion solution using a micro-sampler to obtain a precursor emulsion solution.

Step 4: Into the precursor emulsion solution, 8 ml ethanol was added to demulsify the precursor emulsion solution. The demulsified solution was transferred to a centrifuge tube and was centrifuged at 7000 rpm for 5 minutes. The supernatant was discarded, thereby obtaining a pellet containing a $CH_3NH_3PbBr_3$ perovskite quantum dots material.

Step 5: The pellet containing a $CH_3NH_3PbBr_3$ perovskite quantum dots material was dispersed in n-hexane at a concentration of 3.5 mg/ml. The quantum dots dispersed solution is allowed to stand still at 60 degrees Celsius for 1 hour.

EXAMPLE IX

Preparation of a $CH_3NH_3PbBr_3$ Luminescent Nano-sheet

Step 1: In a 5 ml isotope flask, 0.32 mmol $CH_3NH_3Br$ and 0.3 ml N, N-dimethylformamide were added. The $CH_3NH_3Br$ solution was homogenized using ultrasound. In another 5 ml isotope flask, 0.40 mmol lead bromide and 1.0 ml N, N-dimethylformamide were added. The lead bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the lead bromide solution were drop-wisely added to the emulsion solution using a micro-sampler to obtain a precursor emulsion solution.

Step 4: Into the precursor emulsion solution, 8 ml ethanol was added to demulsify the precursor emulsion solution. The demulsified solution was transferred to a centrifuge tube and was centrifuged at 7000 rpm for 5 minutes. The supernatant was discarded, thereby obtaining a pellet containing a $CH_3NH_3PbBr_3$ perovskite quantum dots material.

Step 5: The pellet containing a $CH_3NH_3PbBr_3$ perovskite quantum dots material was dispersed in n-heptane at a concentration of 2.0 mg/ml. The quantum dots dispersed solution is allowed to stand still at 30 degrees Celsius for 24 hours.

EXAMPLE X

Preparation of a $CH_3NH_3PbBr_3$ Luminescent Nano-sheet

Step 1: In a 5 ml isotope flask, 0.32 mmol $CH_3NH_3Br$ and 0.3 ml N, N-dimethylformamide were added. The $CH_3NH_3Br$ solution was homogenized using ultrasound. In another 5 ml isotope flask, 0.40 mmol lead bromide and 1.0 ml N, N-dimethylformamide were added. The lead bromide solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Br$ solution and the lead bromide solution were drop-wisely added to the emulsion solution using a micro-sampler to obtain a precursor emulsion solution.

Step 4: Into the precursor emulsion solution, 8 ml ethanol was added to demulsify the precursor emulsion solution. The demulsified solution was transferred to a centrifuge tube and was centrifuged at 7000 rpm for 5 minutes. The supernatant was discarded, thereby obtaining a pellet containing a $CH_3NH_3PbBr_3$ perovskite quantum dots material.

Step 5: The pellet containing a $CH_3NH_3PbBr_3$ perovskite quantum dots material was dispersed in toluene at a concentration of 3.5 mg/ml. The quantum dots dispersed solution is allowed to stand still at 30 degrees Celsius for 24 hours.

EXAMPLE XI

Preparation of a $CH_3NH_3CuCl_3$ Luminescent Nano-sheet

Step 1: In a 5 ml isotope flask, 0.32 mmol $CH_3NH_3Cl$ and 0.3 ml N, N-dimethylformamide were added. The $CH_3NH_3Cl$ solution was homogenized using ultrasound. In another 5 ml isotope flask, 0.40 mmol copper chloride and 1.0 ml N, N-dimethylformamide were added. The copper chloride solution was homogenized using ultrasound until a clear solution was obtained.

Step 2: In an isotope flask with a certain capacity, 10 ml n-hexane was added. The isotope flask with the n-hexane was stirred using a magnetic stirrer. Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3Cl$ solution and the copper chloride solution were drop-wisely added to the emulsion solution using a micro-sampler to obtain a precursor emulsion solution.

Step 4: Into the precursor emulsion solution, 8 ml ethanol was added to demulsify the precursor emulsion solution. The demulsified solution was transferred to a centrifuge tube and was centrifuged at 7000 rpm for 5 minutes. The supernatant was discarded, thereby obtaining a pellet containing a $CH_3NH_3CuCl_3$ perovskite quantum dots material.

Step 5: The pellet containing a $CH_3NH_3CuCl_3$ perovskite quantum dots material was dispersed in tetrahydrofuran at a concentration of 3.5 mg/ml. The quantum dots dispersed solution is allowed to stand still at −10 degrees Celsius for 48 hours.

EXAMPLE XII

Preparation of a $CH_3NH_3GeI_3$ Luminescent Nano-sheet

Step 1: In a 5 ml isotope flask, 0.32 mmol $CH_3NH_3I$ and 0.3 ml N, N-dimethylformamide were added. The $CH_3NH_3I$ solution was homogenized using ultrasound. In another 5 ml isotope flask, 0.40 mmol germanium iodine and 1.0 ml N, N-dimethylformamide were added. The germanium iodine solution was homogenized using ultrasound until a clear solution was obtained.

Step 2: In a 10 ml isotope flask an isotope flask with a certain capacity, 10 ml n-hexane was added. The isotope flask with the n-hexane was stirred using a magnetic stirrer.

Oleic acid (0.8 mmol) and dodecylamine (0.12 mmol) were sequentially added into the n-hexane to obtain an emulsion solution.

Step 3: The emulsion solution was stirred using a magnetic stirrer, the $CH_3NH_3I$ solution and the germanium iodine solution were drop-wisely added to the emulsion solution using a micro-sampler to obtain a precursor emulsion solution.

Step 4: Into the precursor emulsion solution, 8 ml ethanol was added to demulsify the precursor emulsion solution. The demulsified solution was transferred to a centrifuge tube and was centrifuged at 7000 rpm for 5 minutes. The supernatant was discarded, thereby obtaining a pellet containing a $CH_3NH_3GeI_3$ perovskite quantum dots material.

Step 5: The pellet containing a $CH_3NH_3GeI_3$ perovskite quantum dots material was dispersed in n-hexane at a concentration of 1.0 mg/ml. The quantum dots dispersed solution is allowed to stand still at 30 degrees Celsius for 72 hours.

EXAMPLE XIII

Characterization of the Luminescent Nano-sheets

The luminescent nano-sheets prepared in Examples I to XII were respectively dispersed in n-hexane. Each dispersed sample was dropped on a carbon support film of a copper mesh, and the sample was examined using a JEM-2100 transmission electron microscope to obtain a TEM photography of the sample.

FIG. 1 is a TEM photography of a luminescent nano-sheet prepared in Example IV. Referring to FIG. 1, the luminescent nano-sheet has a square shape or a rectangular shape. The luminescent nano-sheet has a dimension in a range of 10 nm to 20 nm.

Figure 6:
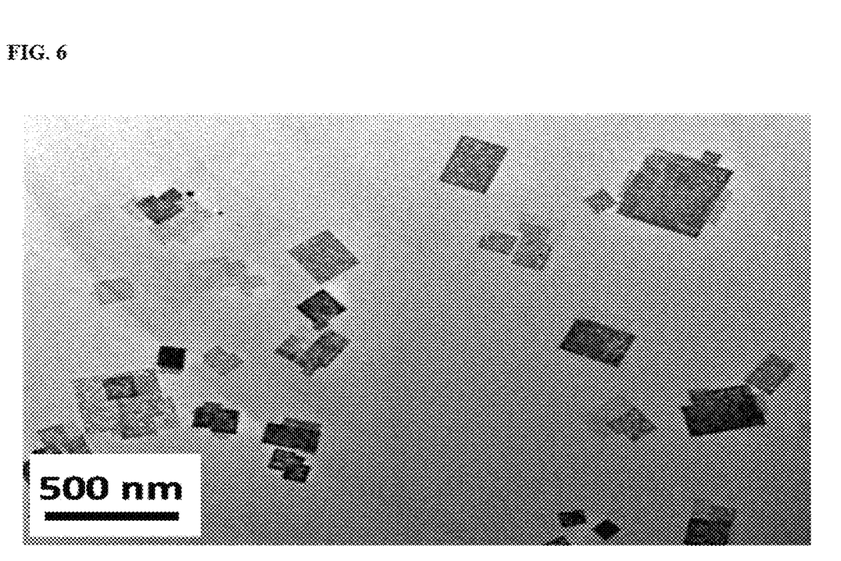
FIG. 6 is a TEM photography of a luminescent nano-sheet prepared in Example XII.

FIG. 6 is a TEM photography of a luminescent nano-sheet prepared in Example XII. The luminescent nano-sheet in FIG. 6 has a square shape or a rectangular shape. The luminescent nano-sheet has a dimension in a range of 10 nm to 500 nm. The surface of the luminescent nano-sheet is substantially free of quantum dots, indicating that the luminescent nano-sheet is of high purity.

EXAMPLE XIV

Absorption and Steady-state Fluorescence Spectroscopy

The luminescent nano-sheets prepared in Examples I to XII were respectively dispersed in n-hexane. Each dispersed sample was examined using a UV-6100 UV-vis spectrophotometer and an F-380 spectrometer, respectively, to obtain absorption and fluorescence spectra. N-hexane was used as control.

Figure 2:
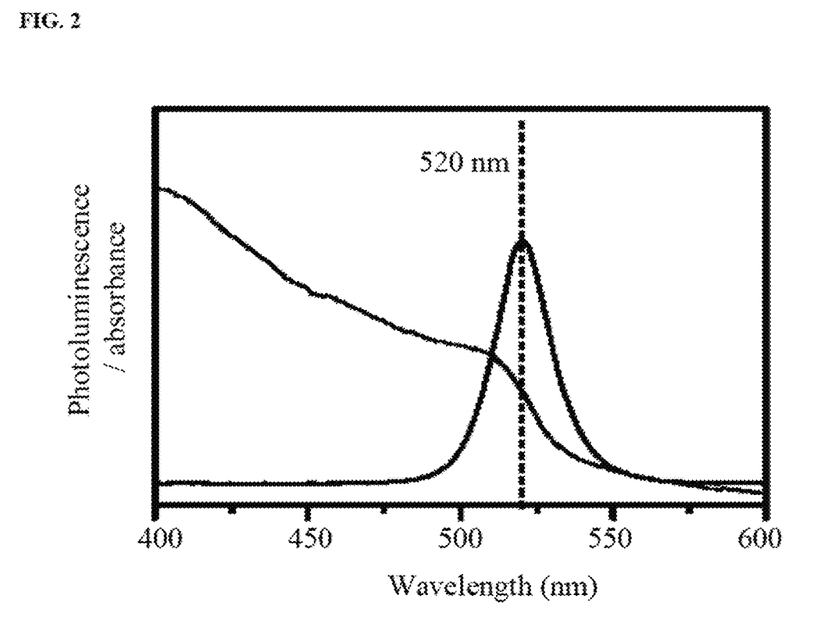
FIG. 2 shows the absorption and fluorescence spectra of the luminescent nano-sheet prepared in Example IV.

FIG. 2 shows the absorption and fluorescence spectra of the luminescent nano-sheet prepared in Example IV. As shown in FIG. 2, the luminescent nano-sheet has an emission peak at 520 nm with a half width of 23 nm.

EXAMPLE XV

Phase Characterization

The luminescent nano-sheets prepared in Examples I to XII were examined using a Rigaku D/max 2500 PC X-ray diffractometer with a scanning range of 10 degrees to 60 degrees at a scanning speed of 1 degree per minute.

Figure 3:
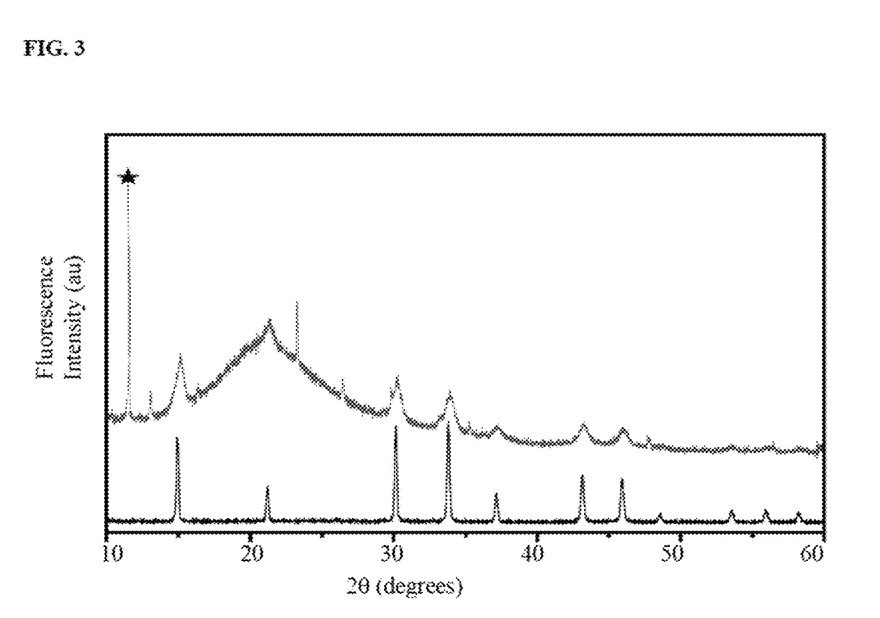
FIG. 3 is an X-ray diffraction pattern of the luminescent nano-sheet prepared in Example IV.

FIG. 3 is an X-ray diffraction pattern of the luminescent nano-sheet prepared in Example IV. The diffraction pattern of the $CH_3NH_3PbBr_3$ luminescent nano-sheet was shown on the top, and the diffraction pattern of an amorphous $CH_3NH_3PbBr_3$ material was shown on the bottom. As shown in FIG. 3, the $CH_3NH_3PbBr_3$ luminescent nano-sheet has a tetragonal crystal phase.

EXAMPLE XVI

Instantaneous Fluorescence Spectroscopy

The luminescent nano-sheets prepared in Examples I to XII were respectively dispersed in n-hexane. Each dispersed sample was drop-coated on a silicon wafer, and excited with a 405 nm laser.

Figure 4:
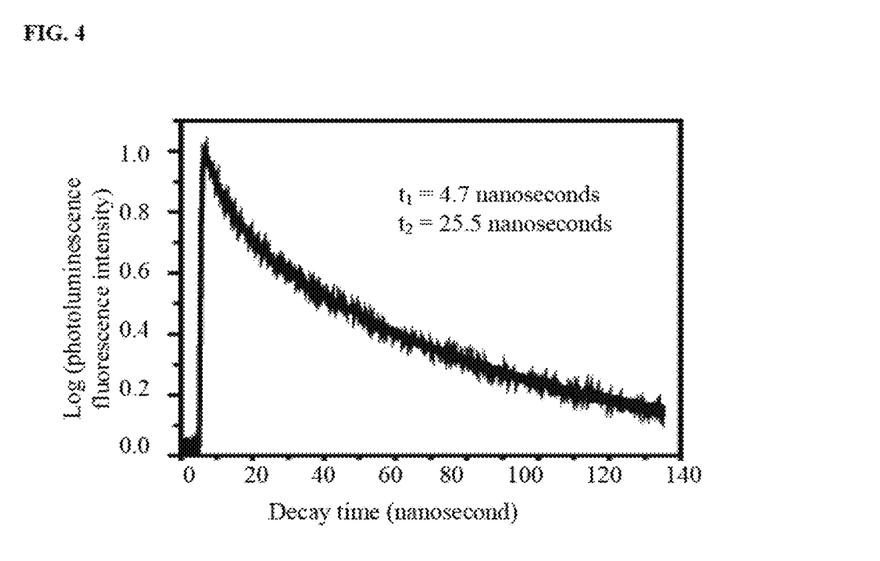
FIG. 4 is an instantaneous fluorescence spectroscopy of the luminescent nano-sheet prepared in Example IV.

FIG. 4 is an instantaneous fluorescence spectroscopy of the luminescent nano-sheet prepared in Example IV. The excited fluorescence has a fluorescence long life $t_2$ of 25.5 nanoseconds, and a fluorescence short life $t_1$ of 4.7 nanoseconds.

EXAMPLE XVII

Characterization of Polarization Characteristics

One gram of 4-methyl-pentene solid particles was dispersed in 10 ml p-xylene. The dispersed solution was heated at a temperature of 120 degrees Celsius for 10 minutes to completely dissolve the 4-methyl-pentene solid particles. The 4-methyl-pentene solution was then rapidly cooled to 50 degrees Celsius. Each of the luminescent nano-sheets prepared in Examples I to XII was added to a separate 4-methyl-pentene solution at 50 degrees Celsius, and the solution was stirred to mix the the luminescent nano-sheet in the 4-methyl-pentene solution.

Each of the mixtures was coated on a glass substrate, and dried in a vacuum oven for 10 minutes to form a film. Each film was stretched along one direction to align the luminescent nano-sheet in the organic matrix. The luminescent nano-sheet film made in this way is conducive to emitting a polarized light.

The luminescent nano-sheet film is excited using laser light having a wavelength of 405 nm. The emitted light was collected by a spectrometer. The detection angle was adjusted between 0 degree and 360 degrees by a polarizing beam splitter.

Figure 5:
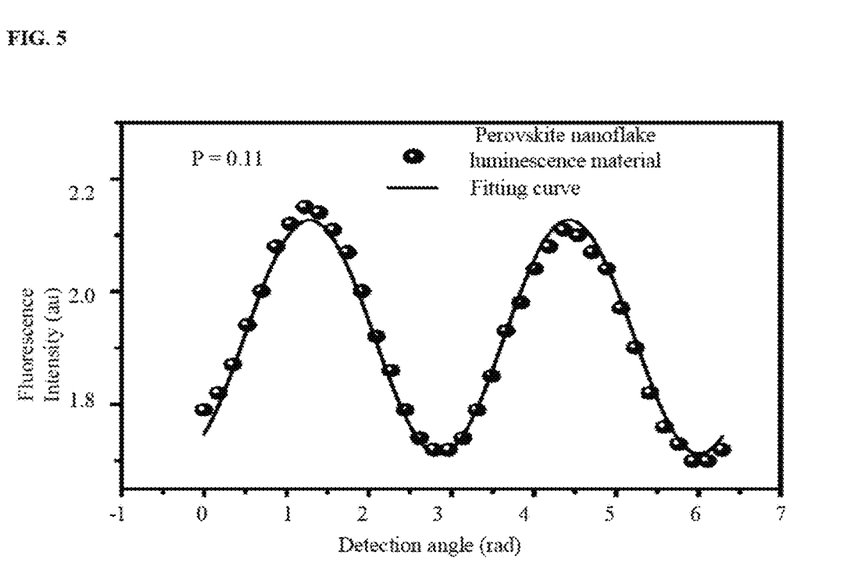
FIG. 5 shows an optical characteristic curve of the polarized light emitted from the luminescent nano-sheet film having a luminescent nano-sheet prepared in Example IV.

FIG. 5 shows an optical characteristic curve of the polarized light emitted from the luminescent nano-sheet film having a luminescent nano-sheet prepared in Example IV. The X-axis in FIG. 5 indicates the detection angle, and the Y-axis indicates the transmitted light intensity.

The degree of polarization of the luminescent nano-sheet film can be calculated according to Equation (1):

$$P=(T1-T2)/(T1+T2) \qquad (1);$$

wherein P stands for the degree of polarization; T1 is a maximum transmitted light intensity; and T2 is a minimum transmitted light intensity.

Based on the results of characterization of the luminescent nano-sheet described herein, a novel high-performance luminescent nano-sheet can be prepared by the methods in the present disclosure. For example, the luminescent nano-sheet can be made to have a thickness in a range of approximately 3 nm to approximately 6 nm, and a width in a range of approximately 10 nm to approximately 1000 nm. The present luminescent nano-sheet has excellent crystallinity, and is capable of stably emitting fluorescent light having a long fluorescence life. Moreover, the present luminescent nano-sheet has very good polarization properties.

The foregoing description of the embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A method of preparing a luminescent nano-sheet, comprising:
   preparing a precursor emulsion solution comprising a metal halide and $RNH_3X$, and having a molar ratio of metal halide to $RNH_3X$ in a range of approximately 0.6 to approximately 0.8;
   demulsifying the precursor emulsion solution to obtain a perovskite quantum dots material and a demulsified solution; and
   forming the luminescent nano-sheet by allowing the perovskite quantum dots material self-assemble into the luminescent nano-sheet;
   wherein X is a halide, R is selected from alkyl, alkenyl, alkynyl, cycloalkyl, cycloalkenyl, cycloalkynyl, aryl, heteroaryl, and heterocyclyl;
   wherein preparing the precursor emulsion solution comprises:
   preparing a $RNH_3X$ solution in a first solvent, the $RNH_3X$ solution having a $RNH_3X$ concentration greater than approximately 0.5 mol/L;
   preparing a metal halide solution in a second solvent, each of the second solvent and the first solvent comprises a same polar solvent;
   dispensing the $RNH_3X$ solution and the metal halide solution into an emulsion solution; and
   homogenizing a mixture comprising the $RNH_3X$ solution, the metal halide solution, and the emulsion solution to obtain the precursor emulsion solution.

2. The method of claim 1, wherein the emulsion solution comprises an organic acid, or an organic amine, or a combination of an organic acid and an organic amine.

3. The method of claim 2, wherein the emulsion solution comprises n-hexane, an organic acid, and an organic amine.

4. The method of claim 1, wherein the $RNH_3X$ solution has a $RNH_3X$ concentration greater than approximately 1.06 mol/L.

5. The method of claim 1, wherein demulsifying the precursor emulsion solution comprises demulsifying the precursor emulsion solution with a demulsifier; and
   the demulsifier comprises acetone, or $C_nH_{2n+1}OH$, $n \geq 1$, or a combination thereof.

6. The method of claim 1, wherein each of the second solvent and the first solvent comprises N, N-dimethylformamide.

7. The method of claim 1, wherein the metal halide comprises germanium halide, tin halide, lead halide, bismuth halide, copper halide, or manganese halide.

8. The method of claim 1, wherein the metal halide comprises lead bromide, the $RNH_3X$ comprises $RNH_3Br$, and the luminescent nano-sheet comprises $RNH_3PbBr_3$.

9. A method of preparing a luminescent nano-sheet, comprising;
   preparing a precursor emulsion solution comprising a metal halide and $RNH_3X$, and having a molar ratio of metal halide to $RNH_3X$ in a range of approximately 0.6 to approximately 0.8;
   demulsifying the precursor emulsion solution to obtain a perovskite quantum dots material and a demulsified solution; and
   forming the luminescent nano-sheet by allowing the perovskite quantum dots material self-assemble into the luminescent nano-sheet
   wherein X is a halide, R is selected from alkyl, alkenyl, alkynyl, cycloalkyl, cycloalkenyl, cycloalkynyl, aryl, heteroaryl, and heterocyclyl;
   wherein forming the luminescent nano-sheet comprises allowing the perovskite quantum dots material to stand in the demulsified solution for a duration equal to or greater than approximately 30 minutes.

10. The method of claim 9, wherein forming the luminescent nano-sheet comprises allowing the perovskite quantum dots material to stand in the demulsified solution at a temperature in a range of approximately −30 degrees Celsius to approximately 70 degrees Celsius.

11. The method of claim 9, wherein demulsifying the precursor emulsion solution comprises demulsifying the precursor emulsion solution with a demulsifier; and
   the demulsifier comprises acetone, or $C_nH_{2n+1}OH$, $n \geq 1$, or a combination thereof.

12. The method of claim 9, wherein the metal halide comprises germanium halide, tin halide, lead halide, bismuth halide, copper halide, or manganese halide.

13. The method of claim 9, wherein the metal halide comprises lead bromide, the $RNH_3X$ comprises $RNH_3Br$, and the luminescent nano-sheet comprises $RNH_3PbBr_3$.

14. A method of preparing a luminescent nano-sheet, comprising:
   preparing a precursor emulsion solution comprising a metal halide and $RNH_3X$, and having a molar ratio of metal halide to $RNH_3X$ in a range of approximately 0.6 to approximately 0.8;

demulsifying the precursor emulsion solution to obtain a perovskite quantum dots material and a demulsified solution;

subsequent to demulsifying the precursor emulsion solution, separating the perovskite quantum dots material from the demulsified solution;

subsequent to separating the perovskite quantum dots material from the demulsified solution, dispersing the perovskite quantum dots material into a non-polar organic solvent; and allowing the perovskite quantum dots material to stand in the non-polar organic solvent for a duration equal to or greater than approximately 30 minutes to self-assemble into the luminescent nano-sheet;

wherein X is a halide, R is selected from alkyl, alkenyl, alkynyl, cycloalkyl, cycloalkenyl, cycloalkynyl, aryl, heteroaryl, and heterocyclyl.

15. The method of claim 14, wherein the non-polar organic solvent comprises one or a combination of toluene, n-hexane, n-heptane, cyclohexane, and tetrahydrofuran.

16. The method of claim 14, wherein dispersing the perovskite quantum dots material into the non-polar organic solvent is performed so that a concentration of the perovskite quantum dots material in the non-polar organic solvent is a range of approximately 1.0 mg/ml to approximately 3.5 mg/ml.

17. The method of claim 14, wherein demulsifying the precursor emulsion solution comprises demulsifying the precursor emulsion solution with a demulsifier; and the demulsifier comprises acetone, or $C_nH_{2n+1}OH$, $n \geq 1$, or a combination thereof.

18. The method of claim 14, wherein the metal halide comprises germanium halide, tin halide, lead halide, bismuth halide, copper halide, or manganese halide.

19. The method of claim 14, wherein the metal halide comprises lead bromide, the $RNH_3X$ comprises $RNH_3Br$, and the luminescent nano-sheet comprises $RNH_3PbBr_3$.

* * * * *